US011990216B2

(12) United States Patent
Guo et al.

(10) Patent No.: US 11,990,216 B2
(45) Date of Patent: *May 21, 2024

(54) DETECTING DISCREPANCIES BETWEEN CLINICAL NOTES AND ADMINISTRATIVE RECORDS

(71) Applicant: International Business Machines Corporation, Armonk, NY (US)

(72) Inventors: Yufan Guo, San Jose, CA (US); David J. Beymer, San Jose, CA (US); Tyler Baldwin, Culver City, CA (US); Vandana Mukherjee, Mountain View, CA (US); Tanveer F. Syeda-Mahmood, Cupertino, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/070,615

(22) Filed: Nov. 29, 2022

(65) Prior Publication Data

US 2023/0095258 A1    Mar. 30, 2023

Related U.S. Application Data

(63) Continuation of application No. 16/514,485, filed on Jul. 17, 2019, now Pat. No. 11,574,713.

(51) Int. Cl.
*G16H 10/60*    (2018.01)
*G06F 16/335*    (2019.01)

(52) U.S. Cl.
CPC ........... *G16H 10/60* (2018.01); *G06F 16/335* (2019.01)

(58) Field of Classification Search
CPC .............................. G16H 10/60; G06F 16/335
See application file for complete search history.

(56) References Cited

U.S. PATENT DOCUMENTS 9,734,297 B2    8/2017 Syeda-Mahmood et al.
9,921,731 B2    3/2018 Finn et al.
(Continued)

FOREIGN PATENT DOCUMENTS

WO    WO2015079353 A1    6/2015

OTHER PUBLICATIONS

List of IBM Patents or Patent Applications Treated as Related, Nov. 29, 2022, 2 pages.

(Continued)

*Primary Examiner* — Eliza A Lam
(74) *Attorney, Agent, or Firm* — Stephen J. Walder, Jr.; Anthony Pallone

(57) ABSTRACT

A mechanism is provided for implement a discrepancy detection mechanism for detecting discrepancies between clinical notes and administrative records. Clinical concepts are extracted from the clinical notes and the administrative records in a patient's electronic medical records (EMRs). The extracted clinical concepts are filtered based on semantic type information to identify concepts that reference diseases or syndromes while also removing negated instances. Utilizing the positive mentions of diseases in clinical notes, the positive mentions of diseases or syndromes in the clinical notes are compared against each positive entry in the administrative records. A discrepancy summary is then generated for diseases or syndromes that failed to translate correctly from clinical notes to the administrative records in the patient's EMRs.

21 Claims, 4 Drawing Sheets

(56) References Cited

U.S. PATENT DOCUMENTS

| | | | |
|---|---|---|---|
| 10,290,370 B2 | 5/2019 | Meystre et al. | |
| 2008/0046286 A1* | 2/2008 | Halsted | G16H 15/00 |
| | | | 705/2 |
| 2008/0133275 A1 | 6/2008 | Haug et al. | |
| 2012/0215559 A1 | 8/2012 | Flanagan et al. | |
| 2016/0239608 A1 | 8/2016 | Cederstrom et al. | |
| 2017/0277856 A1 | 9/2017 | De La Torre et al. | |
| 2018/0107792 A1 | 4/2018 | Rajan et al. | |
| 2018/0293227 A1 | 10/2018 | Guo | |
| 2018/0293494 A1 | 10/2018 | Guo | |
| 2019/0371475 A1* | 12/2019 | Oliveira | G06N 5/01 |
| 2020/0027534 A1* | 1/2020 | Chang | G06F 16/93 |
| 2021/0020277 A1 | 1/2021 | Guo et al. | |

OTHER PUBLICATIONS

Alemzadeh, Homa et al., "An NLP-based cognitive system for disease status identification in electronic health records", Biomedical & Health Informatics (BHI), 2017 IEEE EMBS International Conference on, 4 pages. Dec. 2017.

Cho, Hyejin et al., "A method for named entity normalization in biomedical articles: application to diseases and plants", BMC Bioinformatics (2017) 18:451, 12 pages.

Danadala, Bharath et al., "Scoring Disease-Medication Associations using Advanced NLP, Machine Learning, and Multiple Content Sources", Proceedings of the Fifth Workshop on Building and Evaluating Resources for Biomedical Text Mining (BioTxtM2016), 9 pages. Dec. 2016.

Devarakonda, Murthy et al., "Automated Problem List Generation from Electronic Medical Records in IBM Watson", Twenty-Ninth AAAI Conference on Artificial Intelligence, (AAAI-15), Jan. 25-30, 2015, Austin TX, 6 pages.

Dogan, Rezarta I. et al., "NCBI Disease Corpus: A Resource for Disease Name Recognition and Concept Normalization", Article in Journal of Biomedical Informatics • Jan. 2014, 10 pages.

Farkas, Richard et al., "Automatic construction of rule-based ICD-9-CM coding systems", The Second International Symposium on Languages in Biology and Medicine (LBM) 2007, Singapore. Dec. 6-7, 2007, 9 pages.

Goldstein, IRA et al., "Three Approaches to Automatic Assignment of ICD9-CM Codes to Radiology Reports", In AMIA Annual Symposium Proceedings, vol. 2007, American Medical Informatics Association, Feb. 2007, 5 pages.

Guo, Yufan et al., "Improving the Path from Diagnoses to Documentation: A Cognitive Review Tool for Clinical Notes and Administrative Records", AMIA 2018 Clinical Informatics Conference, May 2018, 9 pages.

High, Rob, "The Era of Cognitive Systems: An Inside Look at IBM Watson and How it Works", IBM Corporation, Redbooks, Dec. 12, 2012, 16 pages.

Neveol, Aurelie et al., "CLEF eHealth 2017 Multilingual Information Extraction task overview: ICD10 coding of death certificates in English and French", In CLEF 2017 Evaluation Labs and Workshop: Online Working Notes, CEUR-WS, Sep. 2017, 17 pages.

Perez, Alicia et al., "Inferred joint multigram models for medical term normalization according to ICD", International Journal of Medical Informatics vol. 110, Feb. 2018, 3 pages, (Abstract Only).

Shmanina, Tatyana et al., "Impact of Corpus Diversity and Complexity on NER Performance", Proceedings of the Australasian Language Technology Association Workshop 2013 (ALTA 2013), Aug. 2013, 5 pages.

Tutubalina, Elena et al., "An Encoder-Decoder Model for ICD-10 Coding of Death Certificates", NIPS 2017 The Thirty-first Annual Conference on Neural Information Processing Systems. Conference Series : Neural Information Processing Systems, Dec. 2017, 6 pages.

Yuan, Michael J., "Watson and healthcare, How natural language processing and semantic search could revolutionize clinical decision support", IBM Corporation, IBM developerWorks, http://www.ibm.com/developerworks/industry/library/ind-watson/, Apr. 12, 2011, 14 pages.

* cited by examiner

DETECTING DISCREPANCIES BETWEEN CLINICAL NOTES AND ADMINISTRATIVE RECORDS

BACKGROUND

The present application relates generally to an improved data processing apparatus and method and more specifically to computer mechanisms for detecting discrepancies between clinical notes and administrative records.

Decision-support systems exist in many different industries where human experts require assistance in retrieving and analyzing information. An example is a diagnosis system employed in the healthcare industry. Diagnosis systems can be classified into systems that use structured knowledge, systems that use unstructured knowledge, and systems that use clinical decision formulas, rules, trees, or algorithms. The earliest diagnosis systems used structured knowledge or classical, manually constructed knowledge bases. The Internist-I system developed in the 1970s uses disease-finding relations and disease-disease relations. The MYCIN system for diagnosing infectious diseases, also developed in the 1970s, uses structured knowledge in the form of production rules, stating that if certain facts are true, then one can conclude certain other facts with a given certainty factor. DXplain, developed starting in the 1980s, uses structured knowledge similar to that of Internist-I, but adds a hierarchical lexicon of findings.

Iliad, developed starting in the 1990s, adds more sophisticated probabilistic reasoning where each disease has an associated a priori probability of the disease (in the population for which Iliad was designed), and a list of findings along with the fraction of patients with the disease who have the finding (sensitivity), and the fraction of patients without the disease who have the finding (1-specificity).

In 2000, diagnosis systems using unstructured knowledge started to appear. These systems use some structuring of knowledge such as, for example, entities such as findings and disorders being tagged in documents to facilitate retrieval. ISABEL, for example, uses Autonomy information retrieval software and a database of medical textbooks to retrieve appropriate diagnoses given input findings. Autonomy Auminence uses the Autonomy technology to retrieve diagnoses given findings and organizes the diagnoses by body system. First CONSULT allows one to search a large collection of medical books, journals, and guidelines by chief complaints and age group to arrive at possible diagnoses. PEPID DDX is a diagnosis generator based on PEPID's independent clinical content.

Clinical decision rules have been developed for a number of medical disorders, and computer systems have been developed to help practitioners and patients apply these rules. The Acute Cardiac Ischemia Time-Insensitive Predictive Instrument (ACI-TIPI) takes clinical and ECG features as input and produces probability of acute cardiac ischemia as output to assist with triage of patients with chest pain or other symptoms suggestive of acute cardiac ischemia. ACI-TIPI is incorporated into many commercial heart monitors/defibrillators. The CaseWalker system uses a four-item questionnaire to diagnose major depressive disorder. The PKC Advisor provides guidance on 98 patient problems such as abdominal pain and vomiting.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory, the at least one memory comprising instructions executed by the at least one processor to cause the at least one processor to implement a discrepancy detection mechanism for detecting discrepancies between clinical notes and administrative records. The illustrative embodiment extracts clinical concepts from the clinical notes and the administrative records in a patient's electronic medical records (EMRs). The illustrative embodiment filters the extracted clinical concepts based on semantic type information to identify concepts that reference diseases or syndromes while also removing negated instances. The illustrative embodiment compares the positive mentions of diseases or syndromes in the clinical notes against each positive entry in the administrative records utilizing the positive mentions of diseases in clinical notes. The illustrative embodiment generates a discrepancy summary for diseases or syndromes that failed to translate correctly from clinical notes to the administrative records in the patient's EMRs.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
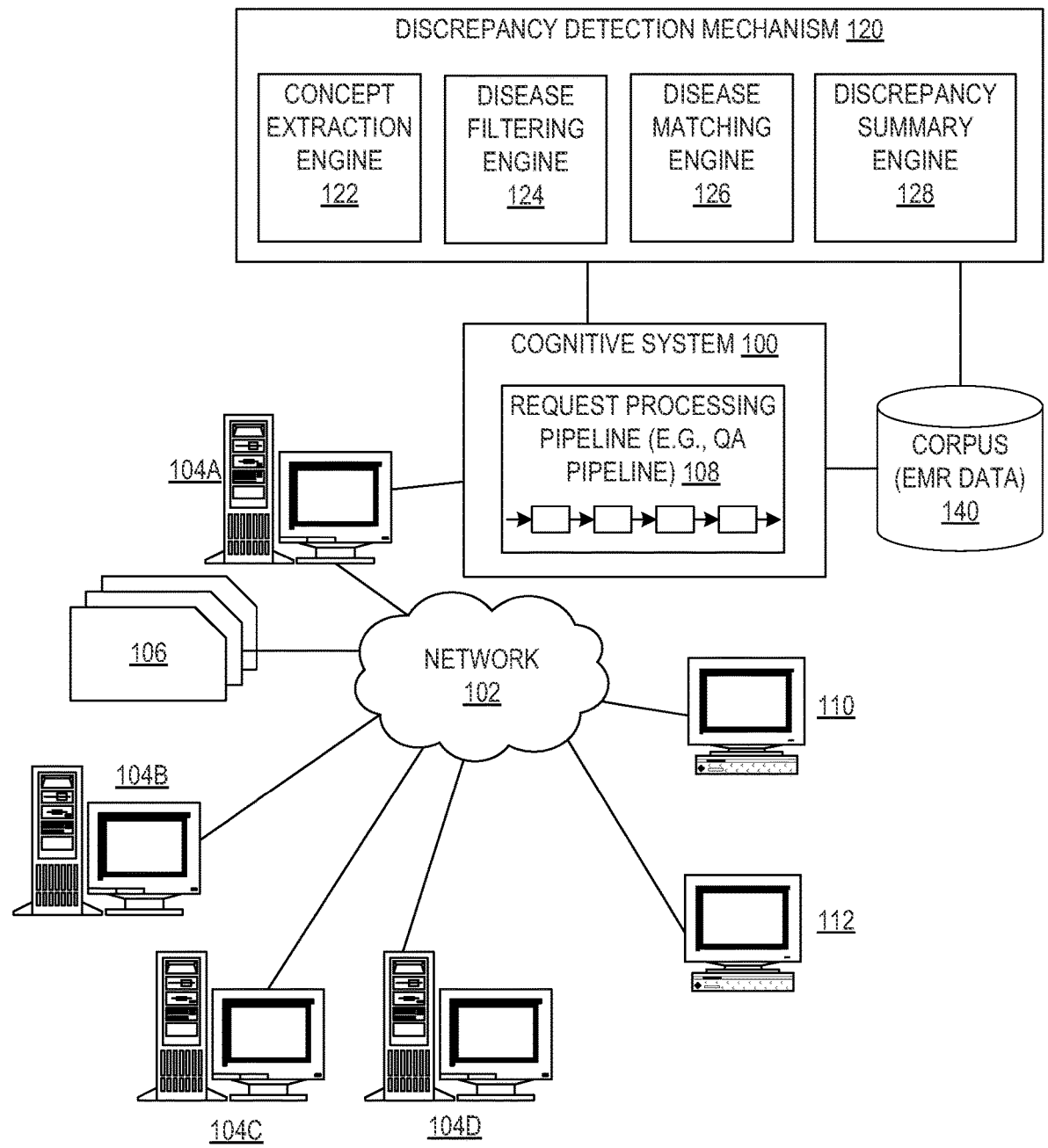
FIG. 1 depicts a schematic diagram of one illustrative embodiment of a cognitive healthcare system in a computer network.

Electronic Medical Record (EMR) or Electronic Health Record (EHR) systems are intended to improve patient-centered care management and hospital administrative processing. However, the information stored in these medical records may be disorganized, incomplete, or inconsistent, creating problems at the patient and system level. That is, the problem-orientated medical record has had a mixture of successes and obstacles in organizing the electronic health record in ways that meaningfully improve clinicians' workflow and quality of patient care. Clinicians commonly review a "problem list" when they encounter a new patient to obtain a quick summary of key clinical issues that are relevant to that patient. However, the clinicians often cannot trust that the information presented is up-to-date, complete, and accurate. On the other hand, the clinicians may also disagree on what the optimal problem list should contain, and may find the problem list to contain much more information than what is required for their immediate clinical roles. Clinicians themselves also contribute to the "problems of the problem list", namely information error propagation and overload. This may come about from inadequate data entry training, or simply as a result of the realities of working in a high-paced multi-disciplinary environment, where not everyone involved in a patient's care feels the onus of updating the problem list after each medical encounter. Finally, inaccuracies in the problem list may propagate to the recorded diagnoses, or vice versa, which in turn may impact hospital systems' billing accuracy and bottom line.

Automatic means of optimizing the problem list using text analytics algorithms has been much researched as a way to address the multitude of "problems of the problem list". One example of this is text analytics algorithms that primarily try to automatically normalize information in free text clinical notes to a structured problem list or recorded diagnosis. However, if this type of algorithm relies on direct secondary use of EMR data without additional careful ground truthing, the algorithm has the disadvantage of being trained with the inherently poor ground truth of the raw structured data in the EMR. Other technologies, either rule-based or machine learning-based, that utilize or train on meticulously annotated ground truth datasets may be able to automatically produce a more reliable problem list from unstructured notes, but these approaches can face challenges of scale and costs.

In order to address the "problems of the problem list," the illustrative embodiments focus on two categories: 1) automatically reconciling the information discrepancies between the free text clinical notes and the structured data (problem list and recorded diagnoses), and 2) automatically prioritizing and summarizing key clinical information to present to clinicians. The illustrative embodiments automatically produces an accurate and up-to-date list of existing patient disease diagnoses and clinically important abnormal findings from free text clinical notes, along with a summary of discrepancies between problem lists and reported diagnoses within administrative records, which helps eliminate data leaks caused by incomplete or incorrect documentation and provides a consistent picture of a patient. Thus, the illustrative embodiments reconcile inconsistencies between clinical diagnoses and administrative records by analyzing free-text notes, problem lists, and recorded diagnoses in real time. The fully-integrated pipeline of the illustrative embodiments provides for efficient, knowledge-driven extraction, normalization, and matching of disease terms among structured and unstructured data. Thus, the illustrative embodiments provide a cognitive data review tool that improves the path from diagnosis to documentation, facilitating accurate and timely clinical and administrative decision-making.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a," "at least one of," and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

As noted above, the present invention provides mechanisms for detecting discrepancies between clinical notes and administrative records. The mechanisms automatically produce an accurate and up-to-date list of existing patient disease diagnoses and clinically important abnormal findings from free text clinical notes, along with a summary of discrepancies between reported diagnoses and administrative records, which help eliminate data leaks caused by incomplete or incorrect documentation and provide a consistent picture of a patient. Thus, the mechanisms reconcile inconsistencies between clinical diagnoses and administrative records by analyzing free-text notes, problem lists, and recorded diagnoses in real time. The fully-integrated pipeline therefore provides for efficient, knowledge-driven extraction, normalization, and matching of disease terms among structured and unstructured data. Thus, the mechanisms provide a cognitive data review tool that improves the path from diagnosis to documentation, facilitating accurate and timely clinical and administrative decision-making.

Figure 2:
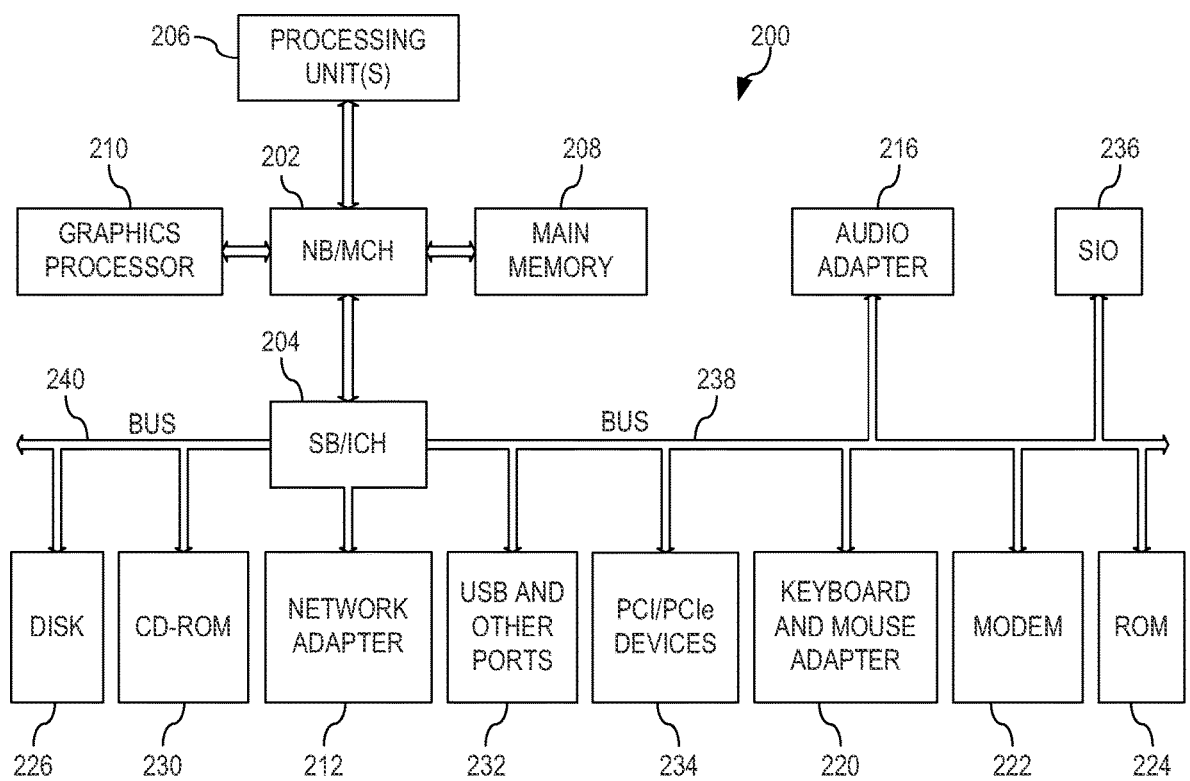
FIG. 2 is a block diagram of an example data processing system in which aspects of the illustrative embodiments are implemented.
Figure 3:
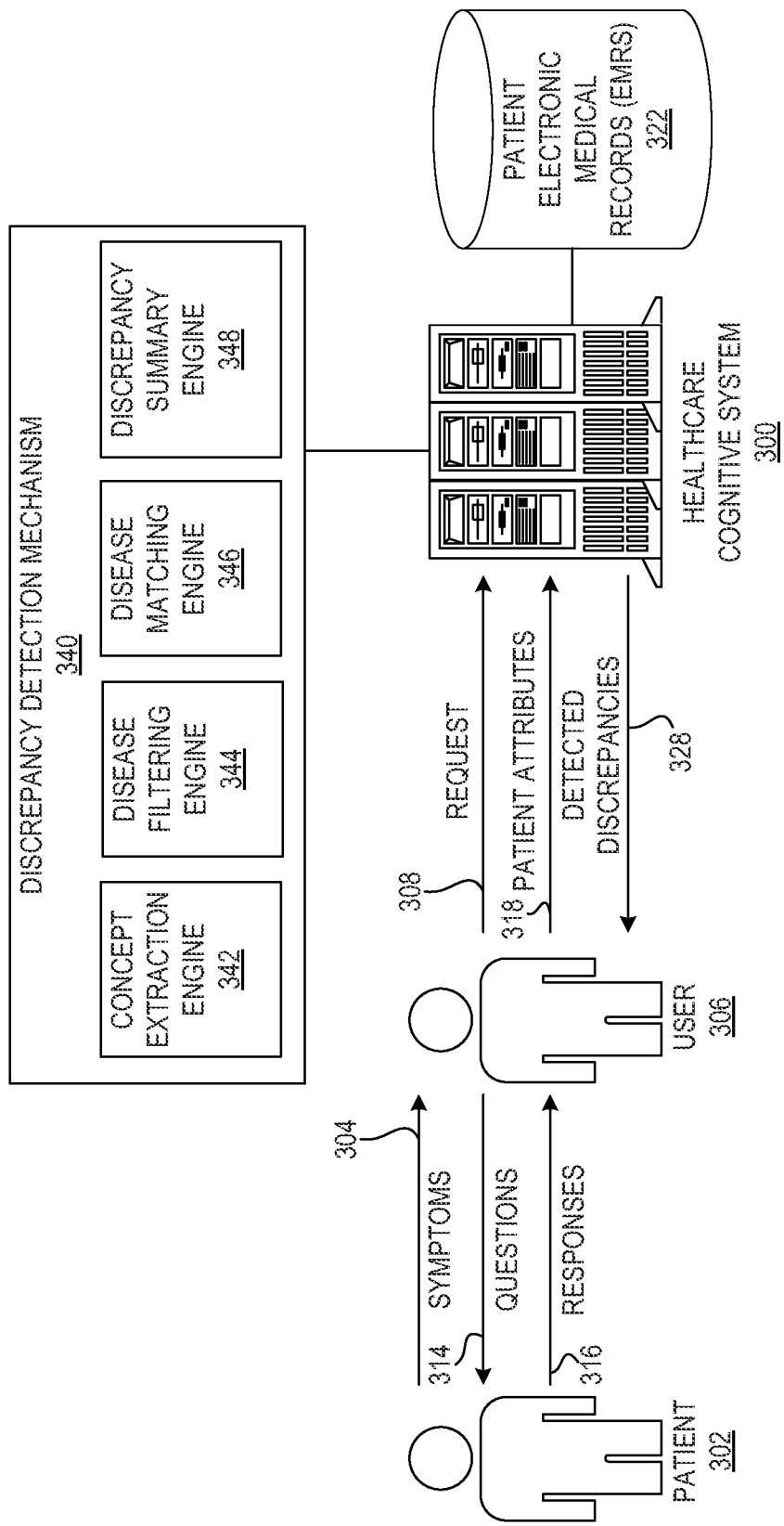
FIG. 3 is an example diagram illustrating an interaction of elements of a healthcare cognitive system in accordance with one illustrative embodiment.

The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structure or unstructured request messages, natural language questions, or any other suitable format for requesting an operation to be performed by the healthcare cognitive system. As described in more detail hereafter, the particular healthcare application that is implemented in the cognitive system of the present invention is a healthcare application for detecting discrepancies between clinical notes and administrative records.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for medical discrepancy detection, another request processing pipeline being configured for patient monitoring, etc.

Moreover, each request processing pipeline may have their own associated corpus or corpora that they ingest and operate on, e.g., one corpus for blood disease domain documents and another corpus for cancer diagnostics domain related documents in the above examples. In some cases, the request processing pipelines may each operate on the same domain of input questions but may have different configurations, e.g., different annotators or differently trained annotators, such that different analysis and potential answers are generated. The healthcare cognitive system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

As noted above, one type of request processing pipeline with which the mechanisms of the illustrative embodiments may be utilized is a Question Answering (QA) pipeline. The description of example embodiments of the present invention hereafter will utilize a QA pipeline as an example of a request processing pipeline that may be augmented to include mechanisms in accordance with one or more illustrative embodiments. It should be appreciated that while the present invention will be described in the context of the cognitive system implementing one or more QA pipelines that operate on an input question, the illustrative embodiments are not limited to such. Rather, the mechanisms of the illustrative embodiments may operate on requests that are not posed as "questions" but are formatted as requests for the cognitive system to perform cognitive operations on a specified set of input data using the associated corpus or corpora and the specific configuration information used to configure the cognitive system. For example, rather than asking a natural language question of "What diagnosis applies to patient P?", the cognitive system may instead receive a request of "generate diagnosis for patient P," or the like. It should be appreciated that the mechanisms of the QA system pipeline may operate on requests in a similar manner to that of input natural language questions with minor modifications. In fact, in some cases, a request may be converted to a natural language question for processing by the QA system pipelines if desired for the particular implementation.

As will be discussed in greater detail hereafter, the illustrative embodiments may be integrated in, augment, and extend the functionality of these QA pipeline, or request processing pipeline, mechanisms of a healthcare cognitive system with regard to detecting discrepancies between clinical notes and administrative records.

Thus, it is important to first have an understanding of how cognitive systems and question and answer creation in a cognitive system implementing a QA pipeline is implemented before describing how the mechanisms of the illustrative embodiments are integrated in and augment such cognitive systems and request processing pipeline, or QA pipeline, mechanisms. It should be appreciated that the mechanisms described in FIGS. 1-3 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, detecting discrepancies between clinical notes and administrative records, and other types of detection generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

Navigate the complexities of human language and understanding.
Ingest and process vast amounts of structured and unstructured data.
Generate and evaluate hypothesis.
Weigh and evaluate responses that are based only on relevant evidence.
Provide situation-specific advice, insights, and guidance.
Improve knowledge and learn with each iteration and interaction through machine learning processes.
Enable decision making at the point of impact (contextual guidance).
Scale in proportion to the task.
Extend and magnify human expertise and cognition.
Identify resonating, human-like attributes and traits from natural language.
Deduce various language specific or agnostic attributes from natural language.
High degree of relevant recollection from data points (images, text, voice) (memorization and recall).
Predict and sense with situational awareness that mimic human cognition based on experiences.
Answer questions based on natural language and specific evidence.

As another example, Watson Health™ Imaging Clinical Review is a retrospective AI-enabled data review tool that helps support a reliable patient record in order to drive accurate, timely, and coordinated care decisions. It highlights both primary diagnoses and incidental findings for a more comprehensive patient problem list, which may help limit the need to re-test patients. This is a tool for clinicians to use to keep the patient's problem list up-to-date throughout his or her care journey.

In one aspect, cognitive systems provide mechanisms for answering questions posed to these cognitive systems using a Question Answering pipeline or system (QA system) and/or process requests which may or may not be posed as natural language questions. The QA pipeline or system is an artificial intelligence application executing on data processing hardware that answers questions pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to cognitive system which implements the QA pipeline. The QA pipeline then answers the input questions using the content in the corpus of data by evaluating documents, sections of documents, portions of data in the corpus, or the like. When a process evaluates a given section of a document for semantic content, the process can use a variety of conventions to query such document from the QA pipeline, e.g., sending the query to the QA pipeline as a well-formed question which is then interpreted by the QA pipeline and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the QA pipeline receives an input question, parses the question to extract the major features of the question, uses the extracted features to formulate queries, and then applies those queries to the corpus of data. Based on the application of the queries to the corpus of data, the QA pipeline generates a set of hypotheses, or candidate answers to the input question, by looking across the corpus of data for portions of the corpus of data that have some potential for containing a valuable response to the input question. The QA pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response, i.e. candidate answer, is inferred by the question. This process is repeated for each of the candidate answers until the QA pipeline identifies candidate answers that surface as being significantly stronger than others and thus, generates a final answer, or ranked set of answers, for the input question.

As mentioned above, QA pipeline mechanisms operate by accessing information from a corpus of data or information (also referred to as a corpus of content), analyzing it, and then generating answer results based on the analysis of this data. Accessing information from a corpus of data typically includes: a database query that answers questions about what is in a collection of structured records, and a search that delivers a collection of document links in response to a query against a collection of unstructured data (text, markup language, etc.). Conventional question answering systems are capable of generating answers based on the corpus of data and the input question, verifying answers to a collection of questions for the corpus of data, correcting errors in digital text using a corpus of data, and selecting answers to questions from a pool of potential answers, i.e. candidate answers.

Content creators, such as article authors, electronic document creators, web page authors, document database creators, and the like, determine use cases for products, solutions, and services described in such content before writing their content. Consequently, the content creators know what questions the content is intended to answer in a particular topic addressed by the content. Categorizing the questions, such as in terms of roles, type of information, tasks, or the like, associated with the question, in each document of a corpus of data allows the QA pipeline to more quickly and efficiently identify documents containing content related to a specific query. The content may also answer other questions that the content creator did not contemplate that may be useful to content users. The questions and answers may be verified by the content creator to be contained in the content for a given document. These capabilities contribute to improved accuracy, system performance, machine learning, and confidence of the QA pipeline. Content creators, automated tools, or the like, annotate or otherwise generate metadata for providing information useable by the QA pipeline to identify these questions and answer attributes of the content.

Operating on such content, the QA pipeline generates answers for input questions using a plurality of intensive analysis mechanisms which evaluate the content to identify the most probable answers, i.e. candidate answers, for the input question. The most probable answers are output as a ranked listing of candidate answers ranked according to their relative scores or confidence measures calculated during evaluation of the candidate answers, as a single final answer having a highest ranking score or confidence measure, or which is a best match to the input question, or a combination of ranked listing and final answer.

FIG. 1 depicts a schematic diagram of one illustrative embodiment of a cognitive system 100 implementing a request processing pipeline 108, which in some embodiments may be a question answering (QA) pipeline, in a computer network 102. For purposes of the present description, it will be assumed that the request processing pipeline 108 is implemented as a QA pipeline that operates on structured and/or unstructured requests in the form of input questions. One example of a question processing operation which may be used in conjunction with the principles described herein is described in U.S. Patent Application Publication No. 2011/0125734, which is herein incorporated by reference in its entirety. The cognitive system 100 is implemented on one or more computing devices 104A-D (comprising one or more processors and one or more memories, and potentially any other computing device elements generally known in the art including buses, storage devices, communication interfaces, and the like) connected to the computer network 102. For purposes of illustration only, FIG. 1 depicts the cognitive system 100 being implemented on computing device 104A only, but as noted above the cognitive system 100 may be distributed across multiple computing devices, such as a plurality of computing devices 104A-D. The network 102 includes multiple computing devices 104A-D, which may operate as server computing devices, and 110-112 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 100 and network 102 enables question processing and answer generation (QA) functionality for one or more cognitive system users via their respective computing devices 110-112. In other embodiments, the cognitive system 100 and network 102 may provide other types of cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 100 may be used with components, systems, subsystems, and/or devices other than those that are depicted herein.

The cognitive system 100 is configured to implement a request processing pipeline 108 that receive inputs from various sources. The requests may be posed in the form of a natural language question, natural language request for information, natural language request for the performance of a cognitive operation, or the like. For example, the cognitive system 100 receives input from the network 102, a corpus or corpora of electronic documents 106, cognitive system users, and/or other data and other possible sources of input. In one embodiment, some or all of the inputs to the cognitive system 100 are routed through the network 102. The various computing devices 104A-D on the network 102 include access points for content creators and cognitive system users. Some of the computing devices 104A-D include devices for a database storing the corpus or corpora of data 106 (which is shown as a separate entity in FIG. 1 for illustrative purposes only). Portions of the corpus or corpora of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus or corpora of data 106 for use as part of a corpus of data with the cognitive system 100. The document includes any file, text, article, or source of data for use in the cognitive system 100. Cognitive system users access the cognitive system 100 via a network connection or an Internet connection to the network 102, and input questions/requests to the cognitive system 100 that are answered/processed based on the content in the corpus or corpora of data 106. In one embodiment, the questions/requests are formed using natural language. The cognitive system 100 parses and interprets the question/request via a pipeline 108, and provides a response to the cognitive system user, e.g., cognitive system user 110, containing one or more answers to the question posed, response to the request, results of processing the request, or the like. In some embodiments, the cognitive system 100 provides a response to users in a ranked list of candidate answers/responses while in other illustrative embodiments, the cognitive system 100 provides a single final answer/response or a combination of a final answer/response and ranked listing of other candidate answers/responses.

The cognitive system 100 implements the pipeline 108 which comprises a plurality of stages for processing an input question/request based on information obtained from the corpus or corpora of data 106. The pipeline 108 generates answers/responses for the input question or request based on the processing of the input question/request and the corpus or corpora of data 106. The pipeline 108 will be described in greater detail hereafter with regard to FIG. 3.

In some illustrative embodiments, the cognitive system 100 may be the IBM Watson™ cognitive system available from International Business Machines Corporation of Armonk, New York, which is augmented with the mechanisms of the illustrative embodiments described hereafter. As outlined previously, a pipeline of the IBM Watson™ cognitive system receives an input question or request which it then parses to extract the major features of the question/request, which in turn are then used to formulate queries that are applied to the corpus or corpora of data 106. Based on the application of the queries to the corpus or corpora of data 106, a set of hypotheses, or candidate answers/responses to the input question/request, are generated by looking across the corpus or corpora of data 106 for portions of the corpus or corpora of data 106 (hereafter referred to simply as the corpus 106) that have some potential for containing a valuable response to the input question/response (hereafter assumed to be an input question). The pipeline 108 of the IBM Watson™ cognitive system then performs deep analysis on the language of the input question and the language used in each of the portions of the corpus 106 found during the application of the queries using a variety of reasoning algorithms.

The scores obtained from the various reasoning algorithms are then weighted against a statistical model that summarizes a level of confidence that the pipeline 108 of the IBM Watson™ cognitive system 100, in this example, has regarding the evidence that the potential candidate answer is inferred by the question. This process is be repeated for each of the candidate answers to generate ranked listing of candidate answers which may then be presented to the user that submitted the input question, e.g., a user of client computing device 110, or from which a final answer is selected and presented to the user. More information about the pipeline 108 of the IBM Watson™ cognitive system 100 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, cognitive system 100 may provide a cognitive functionality for assisting with healthcare based operations. For example, depending upon the particular implementation, the healthcare based operations may comprise patient diagnostics, discrepancy detection systems, medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a healthcare cognitive system 100 that operates in the medical or healthcare type domains and which may process requests for such healthcare operations via the request processing pipeline 108 input as either structured or unstructured requests, natural language input questions, or the like. In one illustrative embodiment, the cognitive system 100 is a medical record verification system that detects discrepancies between clinical notes and administrative records.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for implementing discrepancy detection mechanism 120 for detecting discrepancies between clinical notes and administrative records. Discrepancy detection mechanism 120 comprises concept extraction engine 122, disease filtering engine 124, disease matching engine 126, and discrepancy summary engine 128.

The fully-integrated analytic pipeline of discrepancy detection mechanism is designed to continuously evaluate retrospective clinical data (i.e., clinical notes) and identify discrepancies in a patient's medical record (i.e., the problem list and recorded diagnoses of the corresponding patient in the patient's electronic medical records (EMR) 140). In order to identify discrepancies between the clinical notes and the problem lists that are clinically important as well as the clinical notes and the recorded diagnoses that are clinically important, concept extraction engine 122 performs a separate knowledge-driven clinical concept extraction from the clinical notes, the problem lists, and the recorded diagnoses in the patient's EMR 140, leveraging various medical vocabularies, such as the widely-used Unified Medical Language System (UMLS) Metathesaurus. Concept extraction engine 122 imposes a novel lexicon-based algorithm with specialized inexact matching of clinical terms in reports, with the capacity of identifying contiguous and non-contiguous concepts without using extra corpus annotations. The algorithm identifies the longest common word sequence for a candidate term and a sentence, where the word sequence may be non-contiguous, but covers a sufficient number of words in the term. In light of the inflection rules in English, a word is considered as a match for another if they share a prefix (the first n letters of a word) of sufficient length, a parameter tunable with respect to the preference for recall vs. precision. The problem formulation is an extension of the traditional longest common subsequence problem and is solvable in polynomial time by dynamic programming.

For example, in the following clinical notes, concept extraction engine 122 identifies the underlined words.

The patient is a 75-year-old female who presents to the emergency room with chest pain and pain that radiates into her mid back as well as her right shoulder. She noted that she had a myocardial infarction back in April, had similar symptoms at that time and apparently had no stents placed by way of old history. She has been on chronic Coumadin therapy because of the DVT.

Thus, concept extraction engine 122 detects both contiguous and non-contiguous concepts through an extension of a Longest Common Subsequence (LCS) at word and term/phrase levels. That is, concept extraction engine 122 detects important medical concepts in text using a knowledge graph that is linked with a concept in graph (e.g., from UMLS).

Once concept extraction engine 122 separately extracts the concepts from the text of the clinical notes, the problem lists, and the recorded diagnoses, disease filtering engine 124 then filters the extracted concepts based on their semantic type information to identify concepts that reference disease or syndromes while also removing negated instances. The presence of a disease term in a report does not necessarily suggest a patient with that disease. Therefore, disease terms that are explicitly or implicitly negated in reports need to be filtered off appropriately. Thus, disease filtering engine 124 employs a deep-parsing based recursive negation detector that captures long-distance negations within a dependency parse tree by iteratively identifying negated words until the detected scope of negation converges. Disease filtering engine 124 is further extended by leveraging a richer set of negation indicators, such as not, no, non, false, absence, free, none, exception, risk, family history, unremarkable, non-restricted, absent, negative, except, without, deny, defer, negate, refuse, resolve, rule, quit, exclude, unlikely, unable, impossible, untypical, or the like, and by refining the rules for recruiting new words into the detected scope of negation with respect to various dependency types. In particular, disease filtering engine 124 utilizes:

Parent node of "no" is negated.
Logical arguments of "not", "never", "none" and "false" are negated.
Child nodes of a negated word are negated.
Logical arguments of a negated word are negated, if there is a predicate compliment dependency between them.
Child nodes of a negated conjunction are negated.

For example, in the following clinical notes, disease filtering engine 124 would identifies concepts that reference disease or syndromes while also removing negated instances so that only the underlined words remain identified.

The patient is a 75-year-old female who presents to the emergency room with chest pain and pain that radiates into her mid back as well as her right shoulder. She noted that she had a myocardial infarction back in April, had similar symptoms at that time and apparently had no stents placed by way of old history. She has been on chronic Coumadin therapy because of the DVT.

Utilizing the positive mentions of diseases in clinical notes, disease matching engine 126 checks the positive mentions of diseases against each positive entry in the problem lists and the recorded diagnoses. Disease matching engine 126 employs an ensemble of disease matching algorithms that take a pair of disease terms as input and assess the equivalence of the terms. In one embodiment, a first algorithm is based on approximate string matching of disease names including their associated UM LS concept names. In an alternative embodiment, a second algorithm utilizes disease term decomposition to better handle long complex disease terms. Using this alternative embodiment, a term such as "aortic valve stenosis with regurgitation" is split into a list of elementary anatomy terms (e.g., "aortic") and core disease descriptions (e.g., "valve insufficiency" and "valve stenosis"), and overlap is calculated across both dimensions. In yet another embodiment, a third algorithm is utilized that takes into account the synonyms of all concepts detected (including those subsumed by other concepts), to investigate the overlap of disease terms at a synset level.

Disease matching engine 126 further employs approximate string matching. In approximate string matching, disease matching engine 126 formulates disease name matching as a second-order longest common subsequence (LCS) problem, where the length of LCS is computed at the term and word levels progressively through dynamic programming Utilizing inputted string arrays, each element may be a word for term-level LCS computation (with the matching term-level LCS threshold of, for example, 0.8), or a token for finer-grained word-level LCS analysis (with the matching word-level LCS threshold of, for example, 0.95).

While a direct comparison might work reasonably well given short, compact disease terms, a large number of entries in the problem lists and the recorded diagnoses may refer to codes, such as International Classification of Diseases, Ninth Revision, Clinical Modification (ICD-9-CM) codes, International Classification of Diseases, Tenth Revision, Clinical Modification (ICD-10-CM) codes, or the like, that may be substantially long and complicated (e.g., "Other specified injury of ulnar artery at wrist and hand level of left arm, initial encounter"), creating challenges for basic string matching algorithms. Therefore, disease matching engine 126 may utilize yet another algorithm that decomposes a disease name into a set of anatomy terms and core disease descriptions so that more targeted matching maybe performed in the two dimensions independently. Similar to the semantic type-based disease filter described previously, an anatomy filter was implemented retaining the following semantic types: "Anatomical Structure", "Embryonic Structure", "Fully Formed Anatomical Structure" "Body System", "Body Part, Organ, or Organ Component" "Tissue", "Body Location or Region", and "Body Space or Junction".

In order to improve the hit rate and avoid redundancy, disease matching engine 126 sends all detected concepts within a disease term, including those subsumed by other concepts, through disease and anatomy filtering, but considers only the elementary units for disease decomposition. For instance, an anatomy phrase that contains a sub phrase that also belongs to an anatomy type is excluded from the final set of normalized terms for follow-up matching in the anatomy dimension. The same applies to the normalized disease descriptions. Disease matching engine 126 considers any disease term as a match for another if the intersection of their anatomy sets and core disease sets is not empty.

Disease matching engine 126 further considers clinical terms that are often used interchangeably in medical records but are given separate concepts in UMLS. Despite the flexibility of a more relaxed matching algorithm based on disease name decomposition, previous implementations are still unable to detect such cases. For instance, "carcinoma (CUI: C0007097)" is a special type of "malignant neoplasm (CUI: C0006826)" that develops from epithelial cells, but both terms are considered interchangeable by most expert annotators, as in, e.g., "recurrent renal cell carcinoma" vs. "malignant neoplasm of unspecified kidney except renal pelvis". Thus, disease matching engine 126 employs a supplementary matching algorithm, with better tolerance to diseases with nearly the same meanings, by examining word synonyms along with the synonyms of any nested concepts. For each disease, disease matching engine 126 compiles a set of unique words (referred to as synset) from the names and synonyms of all (nested) concepts. Disease matching engine 126 then uses a degree of overlap between the synsets of two disease terms as a similarity metric to determine a match. In one illustrative embodiment, a degree of overlap between synsets A and B is defined as:

$$\frac{|A \cap B|}{\min(|A|, |B|)}$$

with the matching degree of overlap threshold of 0.8, tunable for a trade-off between precision and recall.

Thus, discrepancy detection mechanism 120 improves the accuracy of the medical record, thus improving patient safety, clinical follow-up, revenue capture, and overall quality. Discrepancy detection mechanism 120 provides efficient, knowledge-driven concept extraction engine 122 capable of detecting contiguous and noncontiguous clinical terms in free texts. Discrepancy detection mechanism 120 further provides disease filtering engine 124 that examines all extracted concepts to identify disease terms according to their semantic type information, followed by a deep-parsing based negation detector to rule out any negative mentions. Discrepancy detection mechanism 120 additionally provides disease matching engine 126 for the pairwise comparison of diseases detected in clinical notes, problem lists, and recorded diagnoses. Finally, discrepancy detection mechanism 120 provides discrepancy summary engine 128 that generates a discrepancy summary for diagnoses that failed to translate correctly from clinical notes to the problem lists and the recorded diagnoses in the patient's EMR 140.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which, which implements a cognitive system 100 and QA system pipeline 108 augmented to include the additional mechanisms of the illustrative embodiments described hereafter.

In the depicted example, data processing system 200 employs a hub architecture including North Bridge and Memory Controller Hub (NB/MCH) 202 and South Bridge and Input/Output (I/O) Controller Hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a healthcare cognitive system in accordance with one illustrative embodiment. The example diagram of FIG. 3 depicts an implementation of a healthcare cognitive system 300 that is configured to detect discrepancies between clinical notes and administrative records. However, it should be appreciated that this is only an example implementation and other healthcare operations may be implemented in other embodiments of the healthcare cognitive system 300 without departing from the spirit and scope of the present invention.

Moreover, it should be appreciated that while FIG. 3 depicts the patient 302 and user 306 as human figures, the interactions with and between these entities may be performed using computing devices, medical equipment, and/or the like, such that entities 302 and 306 may in fact be computing devices, e.g., client computing devices. For example, the interactions 304, 314, and 316 between the patient 302 and the user 306 may be performed orally, e.g., a doctor interviewing a patient, and may involve the use of one or more medical instruments, monitoring devices, or the like, to collect information that may be input to the healthcare cognitive system 300 as patient attributes 318. Interactions between the user 306, which may be a healthcare practitioner such as a physician, nurse, physician's assistant, lab technician, or any other healthcare worker, and the healthcare cognitive system 300 will be electronic via a user computing device (not shown), such as a client computing device 110 or 112 in FIG. 1, communicating with the healthcare cognitive system 300 via one or more data communication links and potentially one or more data networks.

As shown in FIG. 3, in accordance with one illustrative embodiment, a patient 302 presents symptoms 304 of a medical malady or condition to a user 306, such as a healthcare practitioner, technician, or the like. The user 306 may interact with the patient 302 via a question 314 and response 316 exchange where the user gathers more information about the patient 302, the symptoms 304, and the medical malady or condition of the patient 302. It should be appreciated that the questions/responses may in fact also represent the user 306 gathering information from the patient 302 using various medical equipment, e.g., blood pressure monitors, thermometers, wearable health and activity monitoring devices associated with the patient such as a FitBit™, a wearable heart monitor, or any other medical equipment that may monitor one or more medical characteristics of the patient 302. In some cases such medical equipment may be medical equipment typically used in hospitals or medical centers to monitor vital signs and medical conditions of patients that are present in hospital beds for observation or medical treatment.

In response, the user 306 submits a request 308 to the healthcare cognitive system 300, such as via a user interface on a client computing device that is configured to allow users 306 to submit requests to the healthcare cognitive system 300 in a format that the healthcare cognitive system 300 can parse and process. The request 308 may include, or be accompanied with, information identifying patient attributes 318. These patient attributes 318 may include, for example, an identifier of the patient 302 from which patient EMRs 322 for the patient may be retrieved, demographic information about the patient, the symptoms 304, and other pertinent information obtained from the responses 316 to the questions 314 or information obtained from medical equipment used to monitor or gather data about the condition of the patient 302. Any information about the patient 302 that may be relevant to a cognitive evaluation of the patient by the healthcare cognitive system 300 may be included in the request 308 and/or patient attributes 318.

The healthcare cognitive system 300 provides a cognitive system that is specifically configured to perform an implementation specific healthcare oriented cognitive operation. In the depicted example, this healthcare oriented cognitive operation is directed to providing detected discrepancies 328 to the user 306 to assist the user 306 in the treatment of patient 302 based on their reported symptoms 304 and other information gathered about the patient 302 via the question 314 and response 316 process and/or medical equipment monitoring/data gathering. The healthcare cognitive system 300 operates on the request 308 and patient attributes 318 utilizing information gathered from the patient EMRs 322 associated with the patient 302 to detecting discrepancies between clinical notes and administrative records in the patient EMRs 322.

In accordance with the illustrative embodiments herein, the healthcare cognitive system 300 is augmented to include discrepancy detection mechanism 340 for detecting discrepancies between clinical notes made by the user 306 and administrative records associated with patient 302 stored in patient EMRs 322. Discrepancy detection mechanism 340 comprises concept extraction engine 342, disease filtering engine 344, disease matching engine 346, and discrepancy summary engine 348.

The fully-integrated analytic pipeline of discrepancy detection mechanism is designed to continuously evaluate retrospective clinical data (i.e., clinical notes) made by user 306 and identify discrepancies in a patient's medical record (i.e., the problem list and recorded diagnoses of the corresponding patient in the patient's electronic medical records (EMR) 322). In order to identify discrepancies between the clinical notes and the problem lists that are clinically important as well as the clinical notes and the recorded diagnoses that are clinically important, initially concept extraction engine 342 performs a separate knowledge-driven clinical concept extraction of the clinical notes, the problem lists, and the recorded diagnoses in the patient's EMR 322, leveraging various medical vocabularies, such as the widely-used Unified Medical Language System (UMLS) Metathesaurus. Concept extraction engine 342 imposes a novel lexicon-based algorithm with specialized inexact matching of clinical terms in reports, with the capacity of identifying non-contiguous concepts without using extra corpus annotations. The algorithm identifies the longest common word sequence for a candidate term and a sentence, where the word sequence may be non-contiguous, but has to cover a sufficient number of words in the term. In light of the inflection rules in English, a word is considered as a match for another if they share a prefix (the first n letters of a word) of sufficient length, a parameter tunable with respect to the preference for recall vs. precision. The problem formulation is an extension of the traditional longest common subsequence problem and is solvable in polynomial time by dynamic programming Thus, concept extraction engine 342 detects both contiguous and non-contiguous concepts through an extension of a Longest Common Subsequence (LCS) at word and term/phrase levels. That is, concept extraction engine 342 detects important medical concepts in text using a knowledge graph that is linked with a concept in graph (e.g., from UM LS).

Once concept extraction engine 342 separately extracts the concepts from the text of the clinical notes, the problem lists, and the recorded diagnoses, disease filtering engine 344 then filters the extracted concepts based on their semantic type information to identify concepts that reference disease or syndromes while also removing negated instances. The presence of a disease term in a report does not necessarily suggest a patient with that disease. Therefore, disease terms that are explicitly or implicitly negated in reports need to be filtered off appropriately. Thus, disease filtering engine 344 employs a deep-parsing based recursive negation detector that captures long-distance negations within a dependency parse tree by iteratively identifying negated words until the detected scope of negation converges. Disease filtering engine 344 is further extended by leveraging a richer set of negation indicators, such as not, no, non, false, absence, free, none, exception, risk, family history, unremarkable, non-restricted, absent, negative, except, without, deny, defer, negate, refuse, resolve, rule, quit, exclude, unlikely, unable, impossible, untypical, or the like, and by refining the rules for recruiting new words into the detected scope of negation with respect to various dependency types. In particular, disease filtering engine 344 utilizes:

Parent node of "no" is negated.
Logical arguments of "not", "never", "none" and "false" are negated.
Child nodes of a negated word are negated.
Logical arguments of a negated word are negated, if there is a predicate compliment dependency between them.
Child nodes of a negated conjunction are negated.

Utilizing the positive mentions of diseases in clinical notes, disease matching engine 346 checks the positive mentions of diseases against each positive entry in the problem lists and the recorded diagnoses. Disease matching engine 346 employs an ensemble of disease matching algorithms that take a pair of disease terms as input and assess the equivalence of the terms. In one embodiment, a first algorithm is based on approximate string matching of disease names including their associated UMLS concept names. In an alternative embodiment, a second algorithm utilizes disease term decomposition to better handle long complex disease terms. Using this alternative embodiment, a term such as "aortic valve stenosis with regurgitation" is split into a list of elementary anatomy terms (e.g., "aortic") and core disease descriptions (e.g., "valve insufficiency" and "valve stenosis"), and overlap is calculated across both dimensions. In yet another embodiment, a third algorithm is utilized that takes into account the synonyms of all concepts detected (including those subsumed by other concepts), to investigate the overlap of disease terms at a synset level.

Disease matching engine 346 further employs approximate string matching. In approximate string matching, disease matching engine 346 formulates disease name matching as a second-order longest common subsequence (LCS) problem, where the length of LCS is computed at the term and word levels progressively through dynamic programming Utilizing inputted string arrays, each element may be a word for term-level LCS computation (with the matching term-level LCS threshold of, for example, 0.8), or a token for finer-grained word-level LCS analysis (with the matching word-level LCS threshold of, for example, 0.95).

While a direct comparison might work reasonably well given short, compact disease terms, a large number of entries in the problem lists and the recorded diagnoses may refer to codes, such as International Classification of Diseases, Ninth Revision, Clinical Modification (ICD-9-CM) codes, International Classification of Diseases, Tenth Revision, Clinical Modification (ICD-10-CM) codes, or the like, that may be substantially long and complicated (e.g., "Other specified injury of ulnar artery at wrist and hand level of left arm, initial encounter"), creating challenges for basic string matching algorithms. Therefore, disease matching engine 346 may utilize yet another algorithm that decomposes a disease name into a set of anatomy terms and core disease descriptions so that more targeted matching maybe performed in the two dimensions independently. Similar to the semantic type-based disease filter described previously, an anatomy filter was implemented retaining the following semantic types: "Anatomical Structure", "Embryonic Structure", "Fully Formed Anatomical Structure" "Body System", "Body Part, Organ, or Organ Component" "Tissue", "Body Location or Region", and "Body Space or Junction".

In order to improve the hit rate and avoid redundancy, disease matching engine 346 sends all detected concepts within a disease term, including those subsumed by other concepts, through disease and anatomy filtering, but considers only the elementary units for disease decomposition. For instance, an anatomy phrase that contains a sub phrase that also belongs to an anatomy type is excluded from the final set of normalized terms for follow-up matching in the anatomy dimension. The same applies to the normalized disease descriptions. Disease matching engine 346 considers any disease term as a match for another if the intersection of their anatomy sets and core disease sets is not empty.

Disease matching engine 346 further considers clinical terms that are often used interchangeably in medical records but are given separate concepts in UMLS. Despite the flexibility of a more relaxed matching algorithm based on disease name decomposition, previous implementations are still unable to detect such cases. For instance, "carcinoma (CUI: C0007097)" is a special type of "malignant neoplasm (CUI: C0006826)" that develops from epithelial cells, but both terms are considered interchangeable by most expert annotators, as in, e.g., "recurrent renal cell carcinoma" vs. "malignant neoplasm of unspecified kidney except renal pelvis". Thus, disease matching engine 346 employs a supplementary matching algorithm, with better tolerance to diseases with nearly the same meanings, by examining word synonyms along with the synonyms of any nested concepts. For each disease, disease matching engine 346 compiles a set of unique words (referred to as synset) from the names and synonyms of all (nested) concepts. Disease matching engine 346 then uses a degree of overlap between the synsets of two disease terms as a similarity metric to determine a match. In one illustrative embodiment, a degree of overlap between synsets A and B is defined as:

$$\frac{|A \cap B|}{\min(|A|, |B|)}$$

with the matching degree of overlap threshold of 0.8, tunable for a trade-off between precision and recall.

Thus, discrepancy detection mechanism 340 improves the accuracy of the medical record, thus improving patient safety, clinical follow-up, revenue capture, and overall quality. Discrepancy detection mechanism 340 provides efficient, knowledge-driven concept extraction engine 342 capable of detecting contiguous and noncontiguous clinical terms in free texts. Discrepancy detection mechanism 340 further provides disease filtering engine 344 that examines all extracted concepts to identify disease terms according to their semantic type information, followed by a deep-parsing based negation detector to rule out any negative mentions. Discrepancy detection mechanism 340 additionally provides disease matching engine 346 for the pairwise comparison of diseases detected in clinical notes, problem lists, and recorded diagnoses. Finally, discrepancy detection mechanism 340 provides discrepancy summary engine 348 that generates a discrepancy summary for diagnoses that failed to translate correctly from clinical notes to the problem lists and the recorded diagnoses in the patient's EMR 322, in the form of detected discrepancies 328.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/ or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 4:
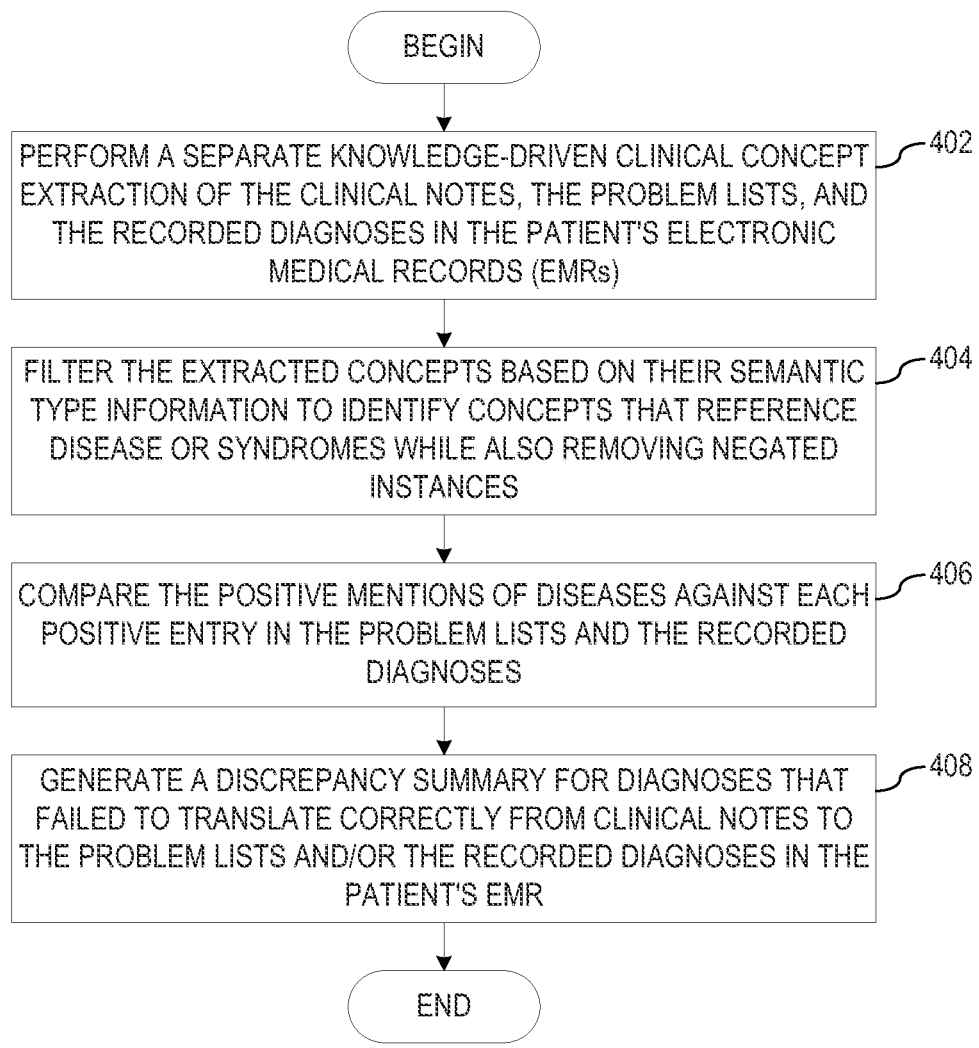
FIG. 4 depicts an exemplary flowchart of the operation performed by a discrepancy detection mechanism in detecting discrepancies between clinical notes and administrative records in accordance with an illustrative embodiment.

FIG. 4 depicts an exemplary flowchart of the operation performed by a discrepancy detection mechanism in detecting discrepancies between clinical notes and administrative records in accordance with an illustrative embodiment. As the operation beings, the concept extraction engine of the discrepancy detection mechanism performs a separate knowledge-driven clinical concept extraction of the clinical notes, the problem lists, and the recorded diagnoses in the patient's electronic medical records (EMRs) in order to identify discrepancies between the clinical notes and the problem lists that are clinically important as well as the clinical notes and the recorded diagnoses that are clinically important (step 402). The concept extraction engine leverages various medical vocabularies, such as the widely-used Unified Medical Language System (UMLS) Metathesaurus. The concept extraction engine imposes a novel lexicon-based algorithm with specialized inexact matching of clinical terms in reports, with the capacity of identifying contiguous and non-contiguous concepts without using extra corpus annotations. The algorithm identifies the longest common word sequence for a candidate term and a sentence, where the word sequence may be non-contiguous, but has to cover a sufficient number of words in the term. In light of the inflection rules in English, a word is considered as a match for another if they share a prefix (the first n letters of a word) of sufficient length, a parameter tunable with respect to the preference for recall vs. precision. The problem formulation is an extension of the traditional longest common subsequence problem and is solvable in polynomial time by dynamic programming Thus, the concept extraction engine detects both contiguous and non-contiguous concepts through an extension of a Longest Common Subsequence (LCS) at word and term/phrase levels. That is, the concept extraction engine detects important medical concepts in text of the clinical notes, the problem lists, and the recorded diagnoses in the patient's (EMRs) using a knowledge graph that is linked with a concept in graph (e.g., from UMLS).

A disease filtering engine of the discrepancy detection mechanism then filters the extracted concepts based on their semantic type information to identify concepts that reference disease or syndromes while also removing negated instances (step 404). The disease filtering engine employs a deep-parsing based recursive negation detector that captures long-distance negations within a dependency parse tree by iteratively identifying negated words until the detected scope of negation converges. The disease filtering engine is further extended by leveraging a richer set of negation indicators, such as not, no, non, false, absence, free, none, exception, risk, family history, unremarkable, non-restricted, absent, negative, except, without, deny, defer, negate, refuse, resolve, rule, quit, exclude, unlikely, unable, impossible, untypical, or the like, and by refining the rules for recruiting new words into the detected scope of negation with respect to various dependency types. In particular, the disease filtering engine utilizes:

Parent node of "no" is negated.
Logical arguments of "not", "never", "none" and "false" are negated.
Child nodes of a negated word are negated.
Logical arguments of a negated word are negated, if there is a predicate compliment dependency between them.
Child nodes of a negated conjunction are negated.

Utilizing the positive mentions of diseases in clinical notes, a disease matching engine of discrepancy detection mechanism compares the positive mentions of diseases against each positive entry in the problem lists and the recorded diagnoses (step 406). The disease matching engine employs an ensemble of disease matching algorithms that take a pair of disease terms as input and assess the equivalence of the terms. In one embodiment, a first algorithm is based on approximate string matching of disease names including their associated UMLS concept names. In an alternative embodiment, a second algorithm utilizes disease term decomposition to better handle long complex disease terms. Using this alternative embodiment, a term such as "aortic valve stenosis with regurgitation" is split into a list of elementary anatomy terms (e.g., "aortic") and core disease descriptions (e.g., "valve insufficiency" and "valve stenosis"), and overlap is calculated across both dimensions. In yet another embodiment, a third algorithm is utilized that takes into account the synonyms of all concepts detected (including those subsumed by other concepts), to investigate the overlap of disease terms at a synset level.

The disease matching engine further employs approximate string matching. In approximate string matching, the disease matching engine formulates disease name matching as a second-order longest common subsequence (LCS) problem, where the length of LCS is computed at the term and word levels progressively through dynamic programming. Utilizing inputted string arrays, each element may be a word for term-level LCS computation (with the matching term-level LCS threshold of, for example, 0.8), or a token for finer-grained word-level LCS analysis (with the matching word-level LCS threshold of, for example, 0.95).

While a direct comparison might work reasonably well given short, compact disease terms, a large number of entries in the problem lists and the recorded diagnoses may refer to codes, such as International Classification of Diseases, Ninth Revision, Clinical Modification (ICD-9-CM) codes, International Classification of Diseases, Tenth Revision, Clinical Modification (ICD-10-CM) codes, or the like, that may be substantially long and complicated (e.g., "Other specified injury of ulnar artery at wrist and hand level of left arm, initial encounter"), creating challenges for basic string matching algorithms. Therefore, the disease matching engine may utilize yet another algorithm that decomposes a disease name into a set of anatomy terms and core disease descriptions so that more targeted matching maybe performed in the two dimensions independently. Similar to the semantic type-based disease filter described previously, an anatomy filter was implemented retaining the following semantic types: "Anatomical Structure", "Embryonic Structure", "Fully Formed Anatomical Structure" "Body System", "Body Part, Organ, or Organ Component" "Tissue", "Body Location or Region", and "Body Space or Junction".

In order to improve the hit rate and avoid redundancy, the disease matching engine sends all detected concepts within a disease term, including those subsumed by other concepts, through disease and anatomy filtering, but considers only the elementary units for disease decomposition. For instance, an anatomy phrase that contains a sub phrase that also belongs to an anatomy type is excluded from the final set of normalized terms for follow-up matching in the anatomy dimension. The same applies to the normalized disease descriptions. The disease matching engine considers any disease term as a match for another if the intersection of their anatomy sets and core disease sets is not empty.

The disease matching engine 346 further considers clinical terms that are often used interchangeably in medical records but are given separate concepts in UM LS. Despite the flexibility of a more relaxed matching algorithm based on disease name decomposition, previous implementations are still unable to detect such cases. For instance, "carcinoma (CUI: C0007097)" is a special type of "malignant neoplasm (CUI: C0006826)" that develops from epithelial cells, but both terms are considered interchangeable by most expert annotators, as in, e.g., "recurrent renal cell carcinoma" vs. "malignant neoplasm of unspecified kidney except renal pelvis". Thus, the disease matching engine employs a supplementary matching algorithm, with better tolerance to diseases with nearly the same meanings, by examining word synonyms along with the synonyms of any nested concepts. For each disease, the disease matching engine compiles a set of unique words (referred to as synset) from the names and synonyms of all (nested) concepts. The disease matching engine then uses a degree of overlap between the synsets of two disease terms as a similarity metric to determine a match. In one illustrative embodiment, a degree of overlap between synsets A and B is defined as:

$$\frac{|A \cap B|}{\min(|A|, |B|)}$$

with the matching degree of overlap threshold of 0.8, tunable for a trade-off between precision and recall. A discrepancy summary engine of the discrepancy detection mechanism then generates a discrepancy summary for diagnoses that failed to translate correctly from clinical notes to the problem lists and/or the recorded diagnoses in the patient's EMR (step 408), with the operation terminating thereafter.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Thus, the illustrative embodiments provide mechanisms for detecting discrepancies between clinical notes and administrative records. The discrepancy detection mechanism improves the accuracy of the medical record, thus improving patient safety, clinical follow-up, revenue capture, and overall quality. The discrepancy detection mechanism provides an efficient, knowledge-driven concept extraction engine capable of detecting contiguous and non-contiguous clinical terms in free texts. The discrepancy detection mechanism further provides a disease filtering engine that examines all extracted concepts to identify disease terms according to their semantic type information, followed by a deep-parsing based negation detector to rule out any negative mentions. The discrepancy detection mechanism additionally provides a disease matching engine for the pairwise comparison of diseases detected in clinical notes, problem lists, and recorded diagnoses. The discrepancy detection mechanism finally provides a discrepancy summary engine that generates a discrepancy summary for diagnoses that failed to translate correctly from clinical notes to the problem lists and/or the recorded diagnoses in the patient's EMR As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions executed by the at least one processor to cause the at least one processor to implement a discrepancy detection mechanism for detecting discrepancies between clinical notes and administrative records, wherein the discrepancy detection mechanism operates to:
    extracting clinical concepts from the clinical notes and the administrative records in a patient's electronic medical records (EMRs) at least by imposing a lexicon-based algorithm with inexact matching of clinical terms with the capacity of identifying contiguous and non-contiguous concepts;
    filtering the extracted clinical concepts based on semantic type information to identify concepts that reference diseases or syndromes while also removing negated instances;
    utilizing the positive mentions of diseases in clinical notes, comparing the positive mentions of diseases or syndromes in the clinical notes against each positive entry in the administrative records; and
    generating a discrepancy summary for diseases or syndromes that failed to translate correctly from clinical notes to the administrative records in the patient's EMRs.

2. The method of claim 1, wherein extracting the clinical concepts from the clinical notes and the administrative records in a patient's EMRs comprises:
    detecting medical concepts in text of the clinical notes and the administrative records using a knowledge graph linked with a concept in graph.

3. The method of claim 1, wherein filtering the extracted clinical concepts based on the semantic type information to identify the concepts that reference diseases or syndromes comprises:
    employing a deep-parsing based recursive negation detector that captures long-distance negations within a dependency parse tree by iteratively identifying negated words until the detected scope of negation converges.

4. The method of claim 1, wherein removing the negated instances from the extracted clinical concepts comprises:
    leveraging a richer set of negation indicators on the extracted clinical concepts; and
    refining rules for recruiting new words into the detected scope of negation with respect to various dependency types.

5. The method of claim 1, wherein comparing the positive mentions of diseases in the clinical notes against each positive entry in the administrative records comprises:
    utilizing disease term decomposition to better handle long complex disease terms.

6. The method of claim 1, wherein comparing the positive mentions of diseases in the clinical notes against each positive entry in the administrative records comprises:
    decomposing a disease name into a set of anatomy terms and core disease descriptions for use in targeted matching.

7. The method of claim 1, wherein comparing the positive mentions of diseases in the clinical notes against each positive entry in the administrative records comprises:
    investigating an overlap of disease names at a synset level taking into account synonyms of all concepts detected.

8. The method of claim 7, wherein in the disease names comprise a set of elementary anatomy terms and core disease descriptions.

9. A computer program product comprising a computer readable storage medium having a computer readable program stored therein, wherein the computer readable program, when executed on a computing device, causes the computing device to implement a discrepancy detection mechanism for detecting discrepancies between clinical notes and administrative records which operates to:
    extract clinical concepts from the clinical notes and the administrative records in a patient's electronic medical records (EMRs) at least by imposing a lexicon-based algorithm with inexact matching of clinical terms with the capacity of identifying contiguous and non-contiguous concepts;
    filter the extracted clinical concepts based on semantic type information to identify concepts that reference diseases or syndromes while also removing negated instances;
    utilizing the positive mentions of diseases in clinical notes, compare the positive mentions of diseases or syndromes in the clinical notes against each positive entry in the administrative records; and
    generate a discrepancy summary for diseases or syndromes that failed to translate correctly from clinical notes to the administrative records in the patient's EMRs.

10. The computer program product of claim 9, wherein the computer readable program to extract the clinical concepts from the clinical notes and the administrative records in a patient's EMRs further causes the computing device to:
    detect medical concepts in text of the clinical notes and the administrative records using a knowledge graph linked with a concept in graph.

11. The computer program product of claim 9, wherein the computer readable program to filter the extracted clinical concepts based on the semantic type information to identify the concepts that reference diseases or syndromes further causes the computing device to:
    employ a deep-parsing based recursive negation detector that captures long-distance negations within a dependency parse tree by iteratively identifying negated words until the detected scope of negation converges.

12. The computer program product of claim 9, wherein the computer readable program to removing the negated instances from the extracted clinical concepts further causes the computing device to:
    leverage a richer set of negation indicators on the extracted clinical concepts; and
    refine rules for recruiting new words into the detected scope of negation with respect to various dependency types.

13. The computer program product of claim 9, wherein the computer readable program to compare the positive mentions of diseases in the clinical notes against each positive entry in the administrative records further causes the computing device to:
utilize disease term decomposition to better handle long complex disease terms.

14. The computer program product of claim 9, wherein the computer readable program to compare the positive mentions of diseases in the clinical notes against each positive entry in the administrative records further causes the computing device to:
decomposing a disease name into a set of anatomy terms and core disease descriptions for use in targeted matching.

15. The computer program product of claim 9, wherein the computer readable program to compare the positive mentions of diseases in the clinical notes against each positive entry in the administrative records further causes the computing device to:
investigate an overlap of disease names at a synset level taking into account synonyms of all concepts detected, wherein in the disease names comprise a set of elementary anatomy terms and core disease descriptions.

16. An apparatus comprising:
a processor; and
a memory coupled to the processor, wherein the memory comprises instructions which, when executed by the processor, cause the processor to implement a discrepancy detection mechanism for detecting discrepancies between clinical notes and administrative records which operates to:
extract clinical concepts from the clinical notes and the administrative records in a patient's electronic medical records (EMRs) at least by imposing a lexicon-based algorithm with inexact matching of clinical terms with the capacity of identifying contiguous and non-contiguous concepts;
filter the extracted clinical concepts based on semantic type information to identify concepts that reference diseases or syndromes while also removing negated instances;
utilizing the positive mentions of diseases in clinical notes, compare the positive mentions of diseases or syndromes in the clinical notes against each positive entry in the administrative records; and
generate a discrepancy summary for diseases or syndromes that failed to translate correctly from clinical notes to the administrative records in the patient's EMRs.

17. A method, in a data processing system comprising at least one processor and at least one memory, the at least one memory comprising instructions executed by the at least one processor to cause the at least one processor to implement a discrepancy detection mechanism for detecting discrepancies between clinical notes and administrative records, wherein the discrepancy detection mechanism operates to:
extracting clinical concepts from the clinical notes and the administrative records in a patient's electronic medical records (EMRs);
filtering the extracted clinical concepts based on semantic type information to identify concepts that reference diseases or syndromes while also removing negated instances at least by employing a deep-parsing based recursive negation detector that captures long-distance negations within a dependency parse tree by iteratively identifying negated words until the detected scope of negation converges;
utilizing the positive mentions of diseases in clinical notes, comparing the positive mentions of diseases or syndromes in the clinical notes against each positive entry in the administrative records; and
generating a discrepancy summary for diseases or syndromes that failed to translate correctly from clinical notes to the administrative records in the patient's EMRs.

18. A method, in a data processing system comprising at least one processor and at least one memory, the at least one memory comprising instructions executed by the at least one processor to cause the at least one processor to implement a discrepancy detection mechanism for detecting discrepancies between clinical notes and administrative records, wherein the discrepancy detection mechanism operates to:
extracting clinical concepts from the clinical notes and the administrative records in a patient's electronic medical records (EMRs);
filtering the extracted clinical concepts based on semantic type information to identify concepts that reference diseases or syndromes while also removing negated instances;
utilizing the positive mentions of diseases in clinical notes, comparing the positive mentions of diseases or syndromes in the clinical notes against each positive entry in the administrative records at least by utilizing disease term decomposition to better handle long complex disease terms; and
generating a discrepancy summary for diseases or syndromes that failed to translate correctly from clinical notes to the administrative records in the patient's EMRs.

19. The method of claim 18, wherein comparing the positive mentions of diseases in the clinical notes against each positive entry in the administrative records comprises:
decomposing a disease name into a set of anatomy terms and core disease descriptions for use in targeted matching.

20. The method of claim 18, wherein comparing the positive mentions of diseases in the clinical notes against each positive entry in the administrative records comprises:
investigating an overlap of disease names at a synset level taking into account synonyms of all concepts detected.

21. The method of claim 20, wherein in the disease names comprise a set of elementary anatomy terms and core disease descriptions.

* * * * *